United States Patent [19]
Freitas

[11] Patent Number: 4,974,583
[45] Date of Patent: Dec. 4, 1990

[54] LEG AND ANKLE BRACE

[75] Inventor: Michael W. Freitas, Irving, Tex.

[73] Assignee: Excell Medical Systems, Inc., Winston Salem, N.C.

[21] Appl. No.: 507,166

[22] Filed: Apr. 10, 1990

[51] Int. Cl.⁵ .............................................. A61F 5/04
[52] U.S. Cl. .............................. 128/80 R; 128/80 F; 128/80 H; 128/83; 128/87 R; 128/590
[58] Field of Search ................. 128/80 R, 68, 80 E, 128/80 F, 80 G, 80 H, 80 J, 590, 83.5, 84 C, 87 R

[56] References Cited

U.S. PATENT DOCUMENTS

| | | | |
|---|---|---|---|
| 2,410,560 | 11/1946 | Witte . | |
| 3,732,861 | 5/1973 | Lehneis | 128/80 E |
| 3,805,773 | 4/1974 | Sichau | 128/80 E |
| 3,850,167 | 11/1974 | Seeley | 128/87 R |
| 4,102,337 | 7/1978 | Golia | 128/80 E |
| 4,136,404 | 1/1979 | Lange | 128/80 R X |
| 4,217,893 | 8/1980 | Payton | 128/89 R |
| 4,280,489 | 7/1981 | Johnson, Jr. | 128/80 H |
| 4,320,748 | 3/1982 | Racette et al. | 128/80 F |
| 4,378,793 | 4/1983 | Mauldin et al. | 128/80 H |
| 4,414,965 | 11/1983 | Mauldin et al. | 128/87 R |
| 4,572,169 | 2/1986 | Mauldin et al. | 128/80 H |
| 4,766,890 | 8/1988 | Hollrah | 128/87 R X |
| 4,771,768 | 9/1988 | Crispin | 128/80 H X |

FOREIGN PATENT DOCUMENTS 1287875  2/1987  U.S.S.R. .......................... 128/80 R

Primary Examiner—Richard J. Apley
Assistant Examiner—Linda C. Maas Dvorak
Attorney, Agent, or Firm—Ross, Howison, Clapp & Korn

[57] ABSTRACT

A fracture brace for leg and ankle treatment includes a shoe having a support surface for supporting the sole of a patient's foot, side walls extending generally perpendicularly to the support surface and an outer sole member. The side walls of the shoe include a receptacle having an outer wall spaced apart from the side wall of the shoe and end walls disposed generally perpendicularly to the shoe side wall and the outer wall. The side walls of the shoe include a spring disposed within the receptacle. The brace further includes side plates each having first and second ends for selective interconnection to the receptacle. The second ends of the side plates are adapted to be received and locked between the spring and the outer wall of the receptacle to prevent removal therefrom.

13 Claims, 2 Drawing Sheets

LEG AND ANKLE BRACE

TECHNICAL FIELD OF THE INVENTION

This invention relates to fracture bracing, and more particularly to a locking mechanism between a side plate and boot of a fracture brace.

BACKGROUND OF THE INVENTION

Traditionally, fractures of the ankle, tibia and fibula have been treated with casts of plaster of paris. The cast immobilizes the ankle, leg, knee and thigh to limit the mobility of the patient. Plaster casts are uncomfortable because of their weight, and lack of ambulation can lead to joint stiffening and muscle atrophy. Therefore, in recent years removable fracture braces or orthosis for tibia and fibula fractures have been used. Such removable braces typically utilize a rigid shoe portion and integrally formed side plates which extend adjacent to the ankle and leg of a patient. The shoe and side plates are then selectively strapped to the foot and leg of the patient.

Due to the various ages and heights of patients, hospitals and doctors are required to inventory numerous sizes of braces to accommodate different sized feet and legs, and in addition are required to stock various sizes of braces depending upon where a fracture occurs on the leg or ankle of a patient. Such inventorying requires a large expenditure of capital as well as physical space for storing such braces of various sizes. Although a physician may inventory a standard shoe size, the requirement for various sized side plates requires the inventorying of numerous braces with the same or different shoe size.

A need has thus arisen for a fracture brace for leg and ankle treatment which provides for separate boot and side plate members which can be independently inventoried by a physician and which can be selectively interconnected to form a rigid fracture brace for a patient. Such a fracture brace will allow for numerous sized boot and side plate members which can be customized to the patient's size as well as the location of the leg fracture.

SUMMARY OF THE INVENTION

In accordance with the present invention, a fracture brace for leg and ankle treatment is provided. The fracture brace includes a shoe having a support surface for supporting the sole of a patient's foot, side walls extending generally perpendicularly to the support surface and an outer sole member. The side walls include an aperture. The brace further includes side plates for selective interconnection to the side walls of the shoe. The side plates are adapted to be received and locked to the side wall apertures to prevent removal therefrom.

In accordance with another aspect of the present invention, a fracture brace for leg and ankle treatment is provided. The brace includes a shoe having a support surface for supporting the sole of a patient's foot, side walls extending generally perpendicularly to the support surface and an outer sole member. The side walls of the shoe include a receptacle having an outer wall spaced apart from the side wall of the shoe and end walls disposed generally perpendicularly to the shoe side wall and the outer wall. The side walls of the shoe include a spring disposed within the receptacle. The brace further includes side plates each having first and second ends for selective interconnection to the receptacle. The second ends of the side plates are adapted to be received and locked between the spring and the outer wall of the receptacle to prevent removal therefrom.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which.

DESCRIPTION OF THE PREFERRED EMBODIMENTS

Figures 1, 2:
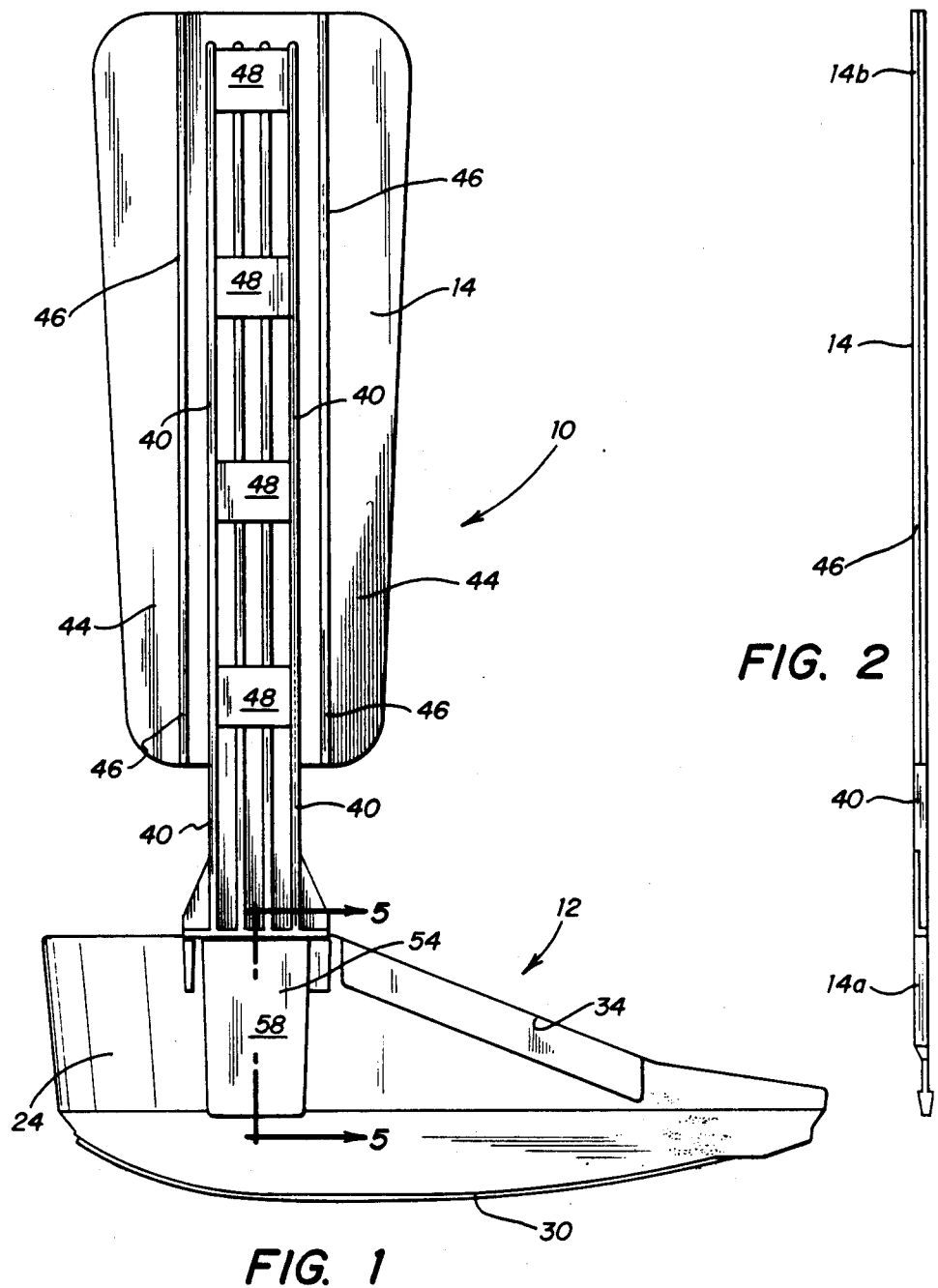
FIG. 1 is a side elevational view of the present fracture brace.
FIG. 2 is an end view of a side plate illustrated in FIG. 1.
Figure 3:
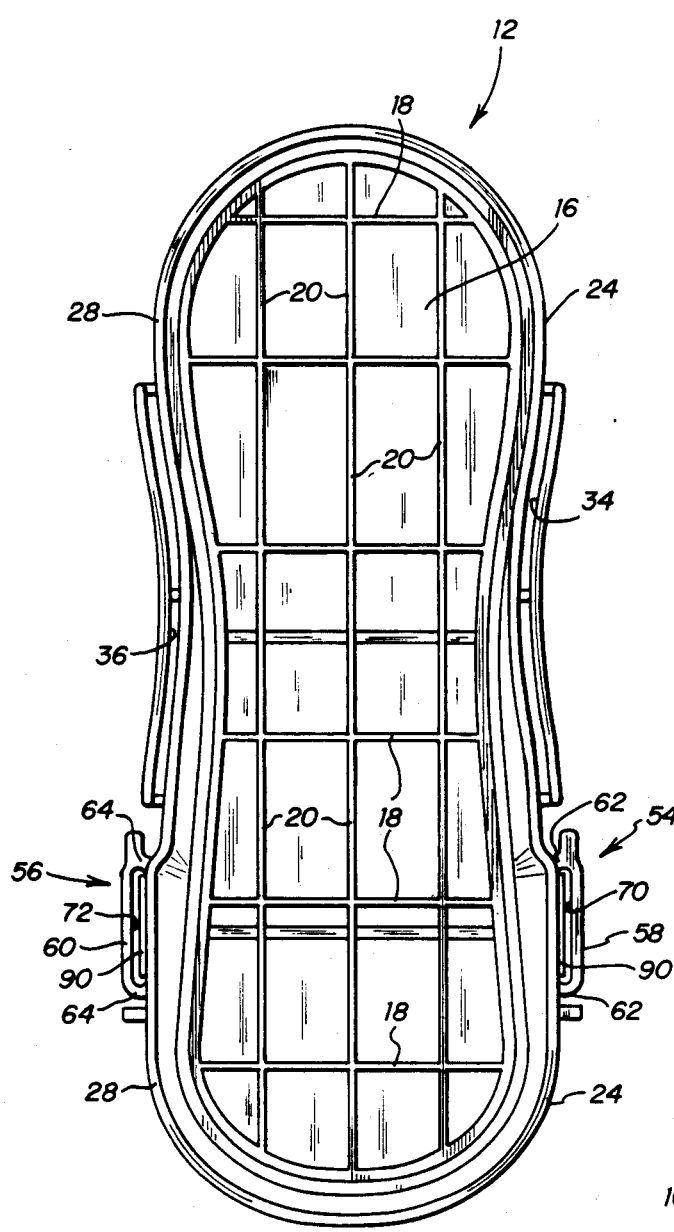
FIG. 3 is a top plan view of the shoe of the present fracture brace illustrated in FIG. 1 with the side plates removed.

Referring simultaneously to FIGS. 1, 2 and 3, the present fracture brace is illustrated, and is generally identified by the numeral 10. Fracture brace 10 may be utilized for treating both tibia and fibula fractures as well as ankle fractures of a patient. Fracture brace 10 includes a shoe, generally identified by the numeral 12, and side plates generally identified by the numeral 14. Although a single side plate 14 is illustrated in FIG. 1, it is understood that a similar side plate is interconnected to the opposite side of shoe 12, such that two side plates 14 are disposed adjacent to the sides of a patient's leg. An important aspect of the present invention is the interconnection between side plates 14 and shoe 12 which allows for the selective interconnection and locking of side plate 14 to shoe 12. In this manner, side plates 14 and shoe 12 can be independently inventoried by a physician to allow for various sizes in both shoe 12 and side plates 14.

Shoe 12 includes a support surface 16 (FIG. 3) formed by ribs 18 and 20 whose edges support layers of plastic or plastic foam (not shown) for receiving the sole of a patient's foot. Shoe 12 further includes side walls 24 and 28 which are perpendicularly disposed to support surface 16 and to an outer sole member 30. Side walls 24 and 28 of shoe 12 further include strap receiving slots 34 and 36, respectively, for receiving straps (not shown) for attaching shoe 12 to the foot of the patient.

Fracture brace 10 includes side plates 14 having ends 14a and 14b. Extending throughout the length of side plates 14 are reinforcing ribs 40. Also disposed on side plates 14 are paddles 44 which are disposed adjacent to the leg of a patient. Paddles 44 include living hinges 46 which allow paddles 44 to curve and conform to the generally circular shape of the leg of a patient. Also disposed on side plates 14 are strap locating areas 48 for receiving straps (not shown) for encircling the leg of a patient for attaching side plates 14 and fracture brace 10 to the patient's leg.

Side walls 24 and 28 of shoe 12 include a receptacle 54 and 56 for receiving end 14a of side plates 14. Receptacles 54 and 56 are fabricated within and extend from side walls 24 and 28 of shoe 12, it being understood that receptacles 54 and 56 may be fabricated interiorly of side walls 24 and 28. Receptacles 54 and 56 include an outer wall 58 and 60, respectively, and end walls 62 and 64 to form slotted apertures 70 and 72 for receiving end 14a of side plates 14.

Figure 4:
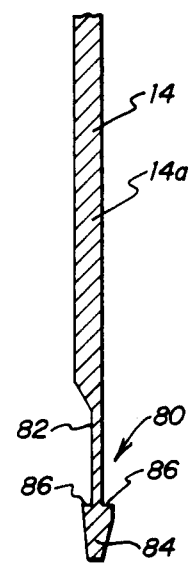
FIG. 4 is an enlarged end view of a side plate illustrated in FIG. 2.
Figure 5:
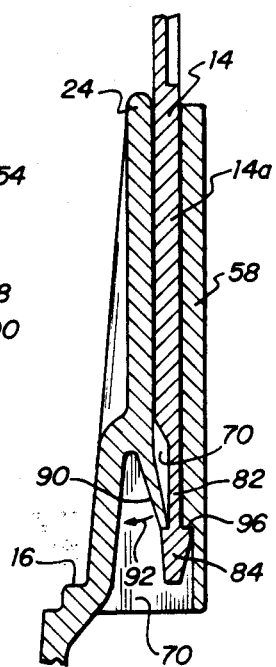
FIG. 5 is a sectional view taken generally along sectional lines 5—5 of FIG. 1 illustrating the insertion of a side plate into the shoe of the present fracture brace.

Referring simultaneously to FIGS. 4 and 5, end 14a of side plates 14 include a locking mechanism, generally identified by the numeral 80. Locking mechanism 80 includes a reduced thickness area 82 and an enlarged thickness area or arrow shaped structure 84. Disposed between areas 82 and 84 are shoulders 86. End 14a of side plates 14 is configured for insertion into apertures 70 and 72 of receptacles 54 and 56, respectively, for locking side plates 14 to shoe 12.

Side wall 24 includes a leaf spring 90 extending from side walls 24 and 28 and disposed within receptacles 54 and 56, respectively. Leaf spring 90 is deformable to bend in the direction of arrow 92 when locking mechanism 80 of side plates 14 is inserted into receptacles 54 and 56. Arrow shaped structure 84 of side plate 14 deflects leaf spring 90 during insertion into receptacles 54 and 56 such that structure 84 slides past leaf spring 90 allowing leaf spring 90 to engage shoulder 86 of locking mechanism 80. Once structure 84 has slid past leaf spring 90, leaf spring 90 returns to its noncompressed position as illustrated in FIG. 5 to prevent the removal of side plate 14 from receptacle 54 and 56. Outer wall 58 of receptacle 54 further includes a shoulder 96 which mates with shoulder 86 to further prevent the removal of side plate 14 from receptacles 54 and 56. Once side plates 14 have been inserted into receptacles 54 and 56 of shoe 12, spring 90 can no longer bend, and therefore side plates 14 are permanently and rigidly interconnected to shoe 12.

It therefore can be seen that the present fracture brace 10 allows for the selective interconnection of side plates to a shoe without the requirement of any external fasteners such as, for example, rivets, bolts or screws while providing for a rigid interconnection between the side plate and shoe. The selective interconnection of side plates and shoes allows a physician to customize fracture braces to the individual needs of a patient in terms of lengths of side plates and shoe sizes thereby providing a patient with a more accurately fitting fracture brace while simultaneously minimizing the amount of inventory to be maintained by the physician.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A fracture brace for leg and ankle treatment of a patient comprising:
    a shoe including a support surface for supporting the sole of the patient's foot, side walls extending generally perpendicularly to said support surface and an outer sole member, said side walls including an aperture;
    side plates each having first and second ends, said second ends thereof for selective interconnection to said side walls of said shoe, said second ends thereof adapted to be received and locked to said side wall apertures to prevent removal therefrom; and
    said side wall apertures including spring means for engaging said second ends of said side plates to prevent removal of said side plates from said apertures.

2. The fracture brace of claim 1 wherein said side plate second ends include locking members for engaging said spring means.

3. The fracture brace of claim 2 wherein said locking members each include:
    a first portion having a first thickness and a second portion having a second thickness being less than said first thickness and a shoulder disposed therebetween, said first portion being engageable with said spring means for temporarily deflecting said spring means upon insertion of said side plate into said side wall aperture, said spring means expanding after said side plate has been fully inserted into said side wall aperture to engage said shoulder.

4. The fracture brace of claim 3 wherein said side wall aperture includes a shoulder for engaging said locking member shoulder.

5. The fracture brace of claim 1 wherein said side plates include hinge means extending along the length thereof for allowing said side plate to conform to the shape of the leg of the patient.

6. The fracture brace of claim 1 wherein said side plates include slots for receiving straps for attaching said side plates to the leg of the patient.

7. The fracture brace of claim 1 wherein said side plates further include ribs extending along the length thereof.

8. A fracture brace for leg and ankle treatment of a patient comprising:
    a shoe including a support surface for supporting the sole of the patient's foot, side walls extending generally perpendicularly to said support surface and an outer sole member;
    a receptacle formed in said side walls, each having an outer wall spaced apart from said shoe side wall and end walls generally perpendicularly disposed to said shoe side wall and said outer wall;
    said shoe side walls including a spring disposed within said receptacles; and
    side plates each having first and second ends, said second ends thereof for selective interconnection to said receptacles, said second ends thereof adapted to be received and locked between said spring and said outer walls to prevent removal from said shoe.

9. The fracture brace of claim 8 wherein said side plates second ends including locking members for engaging said springs.

10. The fracture brace of claim 9 wherein said receptacle outer walls includes shoulder means for engaging said locking members.

11. The fracture brace of claim 8 wherein said side plates further include hinge means extending along the length thereof for allowing said side plates to conform to the shape of the leg of the patient.

12. The fracture brace of claim 11 wherein said side plates further include slots for receiving straps for attaching said side plates to the leg of the patient.

13. The fracture brace of claim 12 wherein said side plates further include a plurality of ribs extending along the length thereof.

* * * * *